United States Patent [19]

Mulder

[11] Patent Number: Plant 6,769

[45] Date of Patent: May 2, 1989

[54] DAHLIA PLANT NAMED MARGARET

[75] Inventor: Alle D. Mulder, Enkhuizen, Netherlands

[73] Assignee: Royal Sluis B.V., Enkhuizen, Netherlands

[21] Appl. No.: 131,371

[22] Filed: Dec. 10, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct Dahlia plant named Margaret, having bright yellow flower color, double flower form, dense foliage, continuous flowering, compact flower bouquet carried above the foliage, compact growth habit, and an adaptability to pot plant or natural outdoor cultures.

1 Drawing Sheet

The present invention relates to a new and distinct cultivar of Dahlia plant known by the cultivar name Margaret, and botanically known as *Dahlia cav.*

Margaret is a sport or mutation of a plant of the commercially well-known seed varieties of Dahlia marketed under the name Figaro. The sport was discovered by applicant in March, 1982 in Enkhuizen, The Netherlands.

The first act of asexual reproduction of Margaret was accomplished when tuberous divisions were taken by me from the new cultivar after discovery in a controlled environment in Enkhuizen, The Netherlands. Subsequent horticultural examination of selected units has demonstrated that the combination of characteristics as herein disclosed for Margaret are firmly fixed and are retained through successive generations of asexual reproduction.

Margaret has not been observed under all possible environmental conditions. The phenotype may vary significantly with variations in environment such as temperature, light intensity, and day length. The following observations, measurements and comparisons describe plants grown in Enkhuizen, The Netherlands under greenhouse and outdoor conditions which approximate those generally used in commercial practice.

The following traits have been repeatedly observed and are determined to be basic characteristics of Margaret, which in combination distinguish this Dahlia as a new and distinct cultivar:

(1) Intense, bright yellow ray floret color.

(2) Double flower form.

(3) Dense foliage.

(4) Continuous flowering, with the flowers being carried above the foliage in a compact bouquet.

(5) Compact growth habit.

(6) Adaptable to pot plant culture as well as natural outdoor growth.

Relevant cultivars for comparison purposes are the seed varieties marketed under the name Rigoletto, and the varieties of Figaro. In comparison to Rigoletto, Margaret is more compact, has a double flower form, and a more intense yellow ray floret color. Margaret is distinguished from Figaro by its more compact habit, its earlier flowering, and the purity of its yellow ray floret color.

The accompanying color photographic drawing shows typical inflorescence and foliage characteristics of Margaret, with colors being as nearly true as possible with illustrations of this type. The photograph is a perspective view of several potted plants of Margaret.

In the following description color references are made to The Royal Horticultural Society Colour Chart. The color values were determined at Enkhuizen, The Netherlands, and the characteristics noted below are based on plants grown at the same location.

Classification:

*Botanical.*—*Dahlia cav.* cv Margaret. (Group IV, peony flowered, classification of International Dahlia Register, 1969).

*Commercial.*—Dahlia.

Parentage: Mutation of Figaro.

Plant:

*Form.*—Generally round.

*Size.*—15–20 cm in height (from top of pot).

*Growth habit.*—Compact.

*Foliage.*—Size: Medium (according to Group classification noted above). Quantity: Abundant, dense. Color: Dark green. Shape: Narrow, generally ovate, edges lobed. Texture: Relatively dull.

Flowers:

*Form.*—Double.

*Shape.*—Overall inflorescence is generally flat, with petals having blunt or slightly rounded tips.

*Size.*—Individual ray florets approximately 4 cm long and 2 cm wide; overall inflorescence approximately 8 cm in diameter.

*Borne.*—On pedicals which are approximately 7–8 cm in length; top of the pedicel oriented at approximately 90° to the vertical axis of the plant; flowers carried compactly above the foliage.

*Continuity.*—Continuously flowers outdoors after first flower opens.

*Stems.*—Color of both new stem and flowering stem is light green.

*Color.*—Fully open, upper surface 2B. Fully open, under surface 1B. Half open, upper surface 2A. Half open, under surface 1A.

*Reproductive organs.*—Normal.

I claim:

1. A new and distinct cultivar of Dahlia plant named Margaret, as illustrated and described.

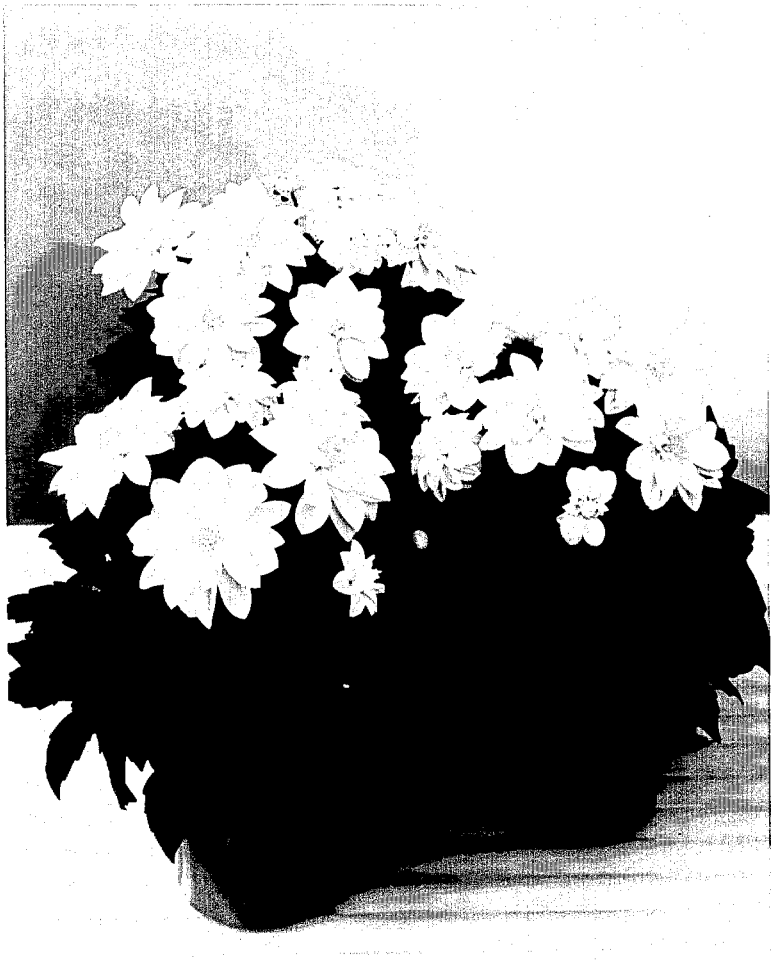

* * * * *